United States Patent
Denner et al.

(10) Patent No.: US 9,526,428 B2
(45) Date of Patent: Dec. 27, 2016

(54) ATTACHMENT FOR A CONTACT LENS AND PRODUCTION METHOD FOR A CONTACT LENS SYSTEM

(71) Applicant: CARL ZEISS MEDITEC AG, Jena (DE)

(72) Inventors: Rene Denner, Reisdorf (DE); Manfred Dick, Gefell (DE); Gerald Kunath-Fandrei, Jena (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 14/399,516

(22) PCT Filed: May 8, 2013

(86) PCT No.: PCT/EP2013/001377
§ 371 (c)(1),
(2) Date: Jan. 14, 2015

(87) PCT Pub. No.: WO2013/167274
PCT Pub. Date: Nov. 14, 2013

(65) Prior Publication Data
US 2015/0157212 A1    Jun. 11, 2015

(30) Foreign Application Priority Data
May 8, 2012 (DE) .................. 10 2012 009 144

(51) Int. Cl.
*A61B 3/00* (2006.01)
*A61B 5/00* (2006.01)
*A61B 3/117* (2006.01)
*A61B 3/10* (2006.01)
*A61N 5/06* (2006.01)
(Continued)

(52) U.S. Cl.
CPC ............... *A61B 5/0095* (2013.01); *A61B 3/10* (2013.01); *A61B 3/117* (2013.01); *A61N 5/0613* (2013.01); *A61N 7/00* (2013.01); *B29D 11/00038* (2013.01); *A61B 2562/143* (2013.01); *A61B 2562/146* (2013.01); *A61N 2005/0648* (2013.01); *B29K 2033/12* (2013.01)

(58) Field of Classification Search
USPC .................................. 351/219, 246
See application file for complete search history.

(56) References Cited

U.S. PATENT DOCUMENTS 4,728,183 A    3/1988  Heacock
7,244,026 B1   7/2007  Ross, III et al.
(Continued)

FOREIGN PATENT DOCUMENTS

CH          694936 A5    9/2005
DE        10135944 A1    2/2003
(Continued)

*Primary Examiner* — Jack Dinh
(74) *Attorney, Agent, or Firm* — Leydig, Voit & Mayer, Ltd.

(57) ABSTRACT

An attachment for a contact lens that comprises a first part provided to be held in position against an eye and a second part connected to the first part. The second part is for fixing the attachment to a contact lens. The first part corresponds to a distal side of a contact lens and forms at least one of a sterile or a disinfected bearing surface for the eye. The second part is configured to connect the attachment to the contact lens and to bring the first part to rest against a distal side of the contact lens.

14 Claims, 4 Drawing Sheets

(51) Int. Cl.
*A61N 7/00* (2006.01)
*B29D 11/00* (2006.01)
*B29K 33/00* (2006.01)

(56) References Cited

U.S. PATENT DOCUMENTS

2003/0032949 A1 2/2003 Schuele et al.
2004/0036839 A1 2/2004 Fischer et al.
2005/0284774 A1 12/2005 Mordaunt

FOREIGN PATENT DOCUMENTS

DE 102009006024 A1 8/2010
EP 1250884 A1 10/2002

ATTACHMENT FOR A CONTACT LENS AND PRODUCTION METHOD FOR A CONTACT LENS SYSTEM

CROSS-REFERENCE TO RELATED APPLICATIONS

This application is a U.S. National Phase application under 35 U.S.C. §371 of International Application No. PCT/EP2013/001377, filed on May 8, 2013, and claims benefit to German Patent Application No. DE 10 2012 009 144.3, filed on May 8, 2012. The International Application was published in German on Nov. 14, 2013, as WO 2013/167274 A1 under PCT Article 21 (2).

FIELD

The present invention relates to opthalmological contact lenses which are used for diagnosis or treatment of eyes, particularly also in connection with therapeutic lasers. The invention further relates to a production method for a contact lens system consisting of a contact lens and an attachment according to the invention.

BACKGROUND

Opthalmological contact lenses are used, for example, for diagnosis or also clinically in conjunction with opthalmological therapeutic lasers. High demands are placed on the contact lenses for basic biocompatibility of the materials on the one hand and also for the level of sterility on the other hand. This relates in principle to all types of contact lenses, in particular those areas which can come into contact with an eye.

U.S. Pat. No. 4,728,183 shows a contact lens which can be used for diagnosis or for laser therapy.

DE 101 35 944 A1 shows a contact lens which can be used in conjunction with a temperature-controlled coagulation laser.

US 2004/0036839 A1 describes a contact lens with a protective cap and an optical functionality.

EP 1 250 884 A1 describes a tonometer contact head with a protective cap with optical transmission and pressure measurement functions, in the scope of tonometry, wherein a static pressure sensor is integrated.

SUMMARY

In an embodiment, the present invention an attachment for a contact lens that comprises a first part provided to be held in position against an eye and a second part connected to the first part. The second part is for fixing the attachment to a contact lens. The first part corresponds to a distal side of a contact lens and forms at least one of a sterile or a disinfected bearing surface for the eye. The second part is configured to connect the attachment to the contact lens and to bring the first part to rest against a distal side of the contact lens.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1A:
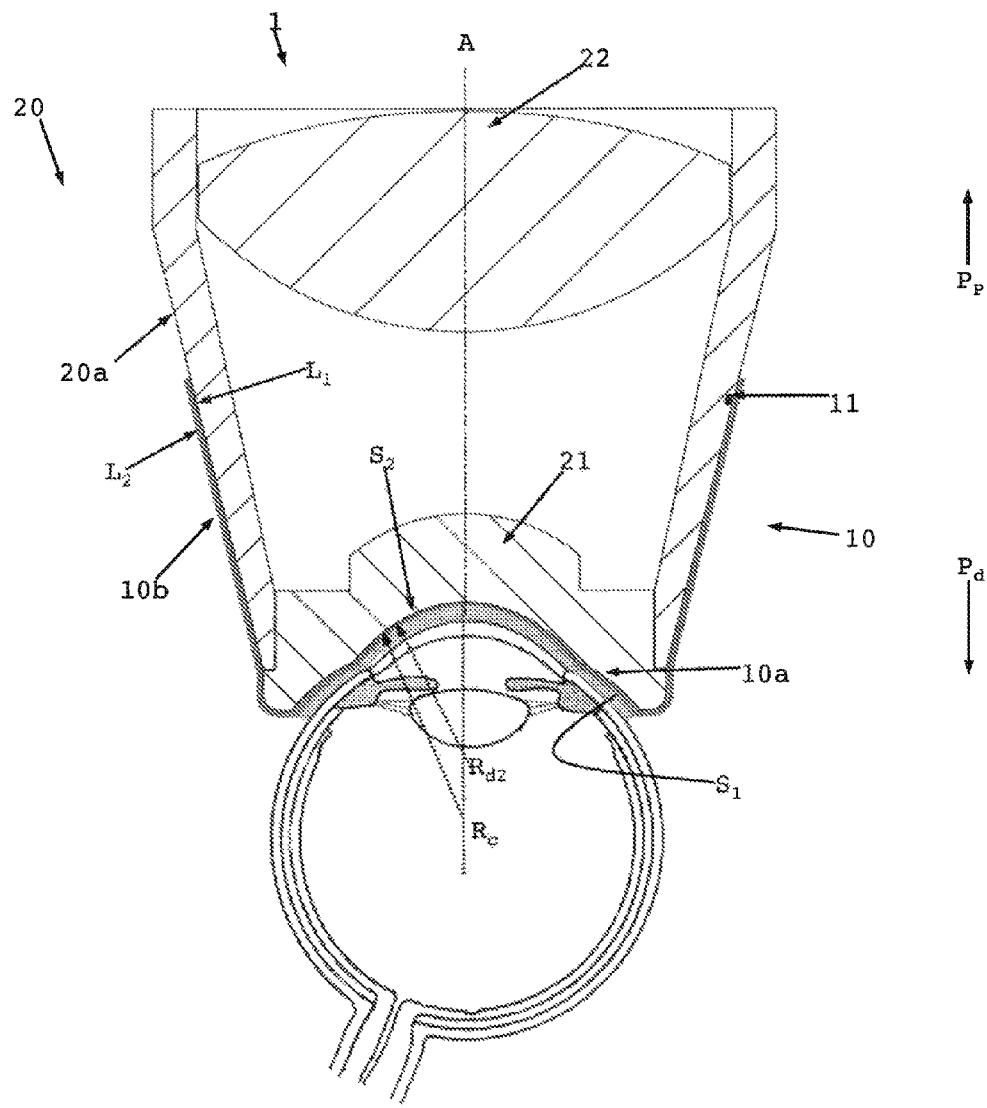
FIG. 1a is a schematic sectional view of an attachment according to a first and third embodiment example of the invention, wherein the attachment is arranged on a contact lens and an eye is in contact with the attachment.

An aspect of the invention is to make it easier to provide contact lenses, in particular sterile or disinfected contact lenses, wherein the contact lenses can be used e.g. in conjunction with a coagulation laser, in particular a temperature-controlled coagulation laser. A contact lens preferably has a high optical and/or acoustic transmission. It is also an aspect of the invention to provide a device and a method in order to be able to use an individual contact lens often and for as long as possible without limitations. Last but not least it is an aspect to reduce the costs of using sterile and/or disinfected contact lenses.

The attachment according to the invention for a contact lens has a first part provided to be held in position against an eye and a second part, connected to the first part, for fixing the attachment to a contact lens, in particular to an optoacoustic contact lens with a (preferably integrated) optoacoustic receiver for eye diagnosis and/or therapy, wherein the first part is designed to correspond to a distal side of a contact lens and to form a sterile and/or disinfected bearing surface for an eye. The second part is designed to connect the attachment to a contact lens and to bring the first part to rest against a distal side of a contact lens.

By means of such an attachment, the high demands for biocompatibility and sterility can be limited to the attachment itself. It is no longer necessary to make the whole contact lens biocompatible or to sterilize or disinfect it. This offers advantages independently of the specific design of a contact lens, especially however e.g. because optionally provided seals between a distal side (e.g. front lens element) and a housing (outer casing surface or lateral surface) of a contact lens no longer have to be sterilized or disinfected or made from a biocompatible material. Rather the seals can now be selected solely with regard to optimal impermeability.

The attachment can preferably be provided for contact lenses that are used as instruments for opthalmological examination and/or treatment. The contact lens can be designed as part of an instrument with an optical and/or acoustic function. The first part can be optically and/or acoustically compatible as it is made from a material which has the same optical and acoustic properties (refractive index, acoustic impedance) as the contact lens. The contact lens can be used for eye diagnosis and/or as an aid for eye therapy. A field of use lies in temperature-controlled coagulation systems for coagulating organic tissue, in particular the retina. For temperature control, the contact lens can be equipped with piezo sensors and an electrical connection to the piezo sensors can be provided, in particular a cable. In the case of such contact lenses it is particularly advantageous if a sterile or disinfected contact lens system can be provided solely by means of a separate sterile attachment, and sterilization of the contact lens itself does not have to be carried out.

In the case of an attachment according to the invention which is used together with a contact lens, materials are preferably used which effect a total optical transmission of more than 85%, particularly preferably more than 95%. Preferably materials are used which lead to such a total transmission for a wavelength range of from 450 nm to 1100 nm, preferably 514 nm to 670 nm, further preferably 523 nm to 670 nm. The attachment then transmits particularly well in this wavelength range.

For the attachment according to the invention with the contact lens materials are preferably used with which a total acoustic transmission of more than 50%, preferably more than 85% can be achieved. Preferably the materials are chosen for a frequency range of from 0.5 MHz to 20 MHz, preferably 0.8 MHz to 1.2 MHz. The attachment then transmits particularly well in this frequency range.

By first part is meant an area or a constituent part of the attachment which, during a use of the attachment, is arranged between an eye of a patient and the contact lens (contact area or contact surface). By second part is meant an area or a constituent part of the attachment to which is assigned primarily the function of connecting the attachment to a contact lens (fixing area or coupling surface). The attachment can be formed substantially only by the first and second part.

By the expression "to bring to rest" is meant a contact between contact lens and attachment such that a surface of the attachment rests at least partially flat against a surface of a contact lens. Connecting the attachment to the contact lens in this way ensures a high optical and acoustic transmission.

By distal side of a contact lens is meant the side which faces away from an operator and faces towards a patient, i.e. the side which in conventional contact lenses is provided to produce the contact with an eye of a patient. The distal side can, e.g., be formed substantially by the surface of a lens element, in particular of a first lens element which, with a second lens element arranged proximal to it, determines the optical beam path within the contact lens. By definition an eye of a patient comes into contact with the distal side of the attachment.

The second part can determine the alignment and arrangement of the first part with reference to the distal side, in particular as a force is exerted by the second part on the first. Particularly preferably the second part is designed such that it can bring the first part to rest against a distal side or lens element under pretensioning. This can be effected e.g. by the second part being loaded with tension and transferring to the first part a tensile force which is so high that the first part can bend elastically slightly in the direction of the tensile force and can nestle up against a lens element and can take on the geometry of the lens element at the interface. Above all in the case of attachments designed shell-like or thin-walled a pretensioning can thereby have the effect that the attachment nestles up against the contour of the distal side of a contact lens and a flat contact is produced via which an undistorted optoacoustic transfer of beams and vibrations between an eye and the contact lens is possible. The flat contact can also be established according to the invention when the first part has a geometry which differs from that of the distal side of a contact lens.

The first and second part can form the attachment as a single-piece component. The second part can be designed as a thin-walled shell which has an outer contour that substantially corresponds to the outer contour of a contact lens, especially in the area in which the second part is intended to come to rest against the contact lens.

The connection between the second part and a contact lens can be a rotation-resistant connection. A screwed connection or a screw connection, a click or snap-on connection or a bayonet-type connection can be provided, or also a combination of these connections. In principle, a connection can also be achieved by means of a clamping ring or a comparable additional connecting means which is coupled to the attachment.

By a screwed connection is meant a connection which is produced by means of at least one additional screw, e.g. a screw which is screwed into a blind hole with an internal thread on the contact lens through a through hole in the second part. By a screw connection is meant a connection which is produced by means of a thread on the attachment itself, thus e.g. an internal thread on the second part which is screwed onto an external thread on the contact lens. A screw connection lends itself above all when the second part is made with a rotationally symmetrical inner surface and the contact lens is made with a rotationally symmetrical outer surface.

The attachment can be designed such that any interference with optical or acoustic properties of the contact lens can be ruled out or at least is not noticeable. This can be ensured in that in any case a flat contact can be established at the interface between the distal side of the contact lens and the proximal side or the first part of the attachment. Optionally liquid can also be introduced at the interface in order more effectively to prevent air gaps or other areas with different refractive indices, wherein the liquid can also be gel-like. The attachment has a high optical and/or acoustic transmission for laser radiation and is also suitable, as mentioned, for the clinical use of opthalmological therapeutic lasers.

A free optical diameter of the attachment is preferably in the range of from 5 to 20 mm, further preferably in the range of from 10 to 14 mm, still further preferably in the region of 12.5 mm. Particularly preferably the free optical diameter is 12.5 mm. By free optical diameter is meant a transmissible area which can be used for the optical imaging without distortions occurring at the edge of the area.

According to an embodiment example the first part has an external diameter which is in the range of from 10 to 30 mm, preferably in the range of from 15 to 25 mm, further preferably in the region of 21 mm. Particularly preferably the external diameter is 21 mm. The external diameter preferably corresponds to a dimension of the distal side of the first part coming to rest against an eye. The external diameter is preferably defined by the outer edges of the first part which can come to rest against an eye and which delimit a transmissible area of the first part.

According to an embodiment example the attachment is designed as a cap which, with the first part and with the second part, can come to rest against a contact lens.

By cap is meant a device which can surround a distal side of a contact lens as well as a lateral surface of a contact lens and can come to rest directly against the contact lens and follows the contour of the contact lens, and rests as closely as possible against it and does not significantly change the actual dimensions of the contact lens. In other words, a contact lens system consisting of contact lens and cap can be handled, stored and transported in the same way as a contact lens without a cap. A cap is also designed such that it remains attached to a contact lens by itself if it is not intended to be removed straightaway. A cap preferably has its own geometry which, although it can also be changed completely, is not to be changed beyond particular dimensions or deformations. The cap can be made rotationally symmetrical in relation to an optical axis of a contact lens.

The cap can be designed as a cap molded to be sheath-like. Such a cap can be designed with substantially the same wall thickness and rests against the contact lens only in a sheath-like manner, like a very thin outer shell. It can be produced simply and cost-effectively by means of injection-molding methods. Depending on the choice of material, the wall thickness can be in the mm range. If e.g. PMMA (polymethyl methacrylate) is chosen as material, a wall thickness e.g. in the region of 1 mm can offer advantages, in particular in respect of an exact resting of the first part against a lens element. The cap can be designed to be thin such that it can be deformed elastically without a large exertion of force and in principle can be called flexible. The cap can be designed such that, when the cap is fitted, the first part is above all under bending stress and the second part is above all under tension, wherein the power of resistance vis-à-vis a bending stress is less than that vis-à-vis tension.

As a result of the second part being able to be under tension and the first part under bending stress, a deformation in the second part can be largely prevented and, in the case of force being transferred from the second part to the first part, only the first part is slightly bent and thereby brought to rest flat, even in the case of an attachment with the same thin wall thickness all over.

The first part (the contact part) can, seen in the proximal direction, have a first concave side S1 and a second convex side S2, wherein the second convex side of the contact part is provided to come to rest against a concave surface of a lens element of a contact lens, and the second convex side can have a radius Rd2 which is smaller than a radius Rc of a concavely formed surface of the lens element. It can hereby be ensured that the first part can be brought to rest against the distal side more and more as force is increasingly applied. Hereby the attachment can be assembled in a way which prevents air pockets: first of all a rather punctiform contact is produced in a central area of a distal side of the contact lens and, as force is increasingly applied by the second part on the first (thus e.g. when the attachment is screwed onto the contact lens) the first part is brought more and more to rest and any air at the interface between contact lens and attachment can escape laterally towards the outside. As air pockets are prevented, it is possible to prevent a jump in or a discontinuity of an acoustic impedance or a jump in or a discontinuity of an optical refractive index from being generated at the individual boundary surfaces. Rather a so-called optical contact or a connection by optical wringing between individual boundary surfaces can be ensured which at the same time also produces a good acoustic contact. A high optical or acoustic transmission can hereby be ensured.

In particular for the case where air pockets cannot be completely prevented at the boundary surfaces or in order to reduce the likelihood of air pockets forming while the attachment is being used, an optically and acoustically compatible immersion fluid and/or a corresponding immersion gel can preferably be introduced between the attachment and a contact lens, with the result that a jump in the refractive index or the impedance can be prevented or at least kept small even in the case where form-fitting contact between attachment and contact lens may possibly not be over the whole surface.

By proximal direction is meant a direction towards an operator or away from a patient to be examined or to be treated, and by distal direction, contrary to this, a direction away from the operator or towards the patient. By definition, an eye of a patient comes into contact with the distal side of the attachment.

In particular the second part (the fixing part) can be connected via an inner casing surface to a lateral surface of a contact lens. For this purpose, an external thread can be provided on the lateral surface and an internal thread can be provided on the inner casing surface of the second part. Optionally or additionally a snap mechanism can be provided.

By means of a thin cap which is elastically deformable in a certain area it can be ensured that the cap can be fixed to a contact lens reversibly and without a special exertion of force in such a way that a distal side or a lens element and a first part of the cap touch each other substantially without gaps. As the cap is made thin-walled, a relatively small pretensioning force is sufficient to ensure that the geometry of the first part matches a curvature of a lens element or a distal side without the need to apply an excessive pretensioning force. At the same time, the pretensioning can ensure a certain stability and a good geometric accuracy and conformity of the boundary surfaces resting against each other. This makes it possible to use the attachment multiple times under the same conditions. Further, it can also be ruled out that any stresses on the attachment in connection with a sterilization then also do lead to an impairment of the functionality of the attachment, should the stresses have led to minimal geometric changes or deformations of the attachment.

Preferably the radius Rd2 can differ from the radius Rc. As a result the contact area of the attachment can be held in position particularly closely against the surface of the contact lens. This difference in the radii, depending on the chosen materials, is preferably 1% to 20%, preferably 3% to 10%. Preferably the radius Rd2 is smaller than the radius Rc.

According to an embodiment example, the attachment is designed as a cap with a first part (contact part) which has a varying thickness in the distal direction.

The thickness can vary in the range of from a few millimeters to a few centimeters. On the one hand, an optical function can hereby be performed by the cap as the cap is designed as part of a lens system of the contact lens. The concave distal side, against which an eye is to come to rest, can thus be formed solely by the shape of the attachment. On the other hand, attachments which have different first concave sides but can nevertheless be coupled to the contact lens in the same way can be provided for a particular type of contact lenses. In this way it is possible e.g. to adapt to greatly differing sizes of eye, e.g. in children and adults.

The thickness of the first part is preferably in the range of from 1 millimeter to 3 centimeters, further preferably in the range of from 1 millimeter to 2 centimeters, particularly preferably in the range of from 3 millimeters to 1 centimeter. Hereby a pretensionable first part can be provided which can also undertake a lens function.

A thickness or wall thickness of the second part is preferably in the range of from 1 to 10 millimeters, further preferably in the range of from 1 to 5 millimeters. The second part can have a constant thickness or wall thickness. In the case of a small thickness, in particular in the region of 1 millimeter, the contact lens even with attachment can be made slim and is also suitable for coming to rest in the case of small eye sockets.

The term thickness is chosen in this connection because an attachment with lens function does not have a wall thickness in the actual sense, but has a thickness specifically with regard to optical or acoustic transmission.

The attachment or the cap can be designed with a solid first part, i.e. a first part produced from solid material. The attachment can optionally entirely consist of or be manufactured from a solid body. A solid attachment can be produced e.g. by turning. A solid contact cap can be separated off in a planar cut e.g. as part of an optomechanical system.

According to an embodiment example, the attachment has a substantially planar proximal side on the first part.

The first part can have a substantially planar proximal side and a concave distal side. Hereby the attachment, as component, can take on at least partially the function of a lens. The interface between contact lens and attachment is therefore formed by two substantially planar surfaces. This can be advantageous at least in that the optical properties of the contact lens system consisting of attachment and contact lens can be better controlled or the number of convex or concave interfaces can be reduced. If in the case of a sheath-like attachment a total of four curved surfaces are provided on the lens element and the attachment, in the case of a substantially planar interface there are only two.

The second part can, as in the case of a sheath-like cap, be connectable e.g. via a screw or snap-on connection to a lateral surface of a contact lens.

A substantially planar side can however also have a slight curvature. A curvature then preferably describes a radius Rd which is at least almost equal to the radius Rc of a distal side of a contact lens, for example of a lens element of a contact lens formed concave on the distal side. However, if the distal side is completely planar, the curvature of the first part can be designed to be so slight that in the case of a certain pretensioning of the first part air gaps at the interface to the distal side of the contact lens can be prevented. In other words, a slightly curved surface of the attachment can be made into a planar surface by means of the pretensioning. A pretensioning is, however, not absolutely necessary but is only a possibility for improving the contact.

In other words, in the case of a substantially planar interface there need not necessarily be two surfaces arranged exactly plane-parallel in relation to each other, rather the lens element or a distal side and/or the attachment can have a very slight curvature, i.e. an extremely large radius can be provided. By this means, a pretensioning can be established more easily. For the case where both surfaces have a very slight curvature, the difference between the radii, if any, is then only minimal, thus is less significant than in the case of a sheath-like attachment. The reason for this is also that a solid lens-like attachment requires a larger force in order to be pretensioned or deformed.

In the case of a solid attachment which also takes on a function as a lens, a difference between a curvature from a distal side and a curvature from the second side of the first part is thus less than in the case of a thin-walled shell-like attachment. In a solid attachment, even in the case of a minimal difference in the curvatures, a sufficiently large pretensioning can be achieved. However, it may be mentioned that, although a pretensioning is desirable, it is not necessary in all circumstances for the contact lens to function correctly. In principle, a liquid can be provided at the interface between contact lens and attachment, e.g. to further improve the optical properties, irrespective of whether a pretensioning force has been established or not. A pretensioning force can, however, lead to an additional liquid being unnecessary.

According to an embodiment example, the attachment has, in the first part, a wall thickness which is smaller than 10 millimeters.

Such a comparatively thin-walled first part can be pretensioned in a particularly easy way and brought to rest completely flat against the distal side. The thickness of the first part (contact part) of the attachment is preferably less than 20 millimeters, preferably in the range of from 0.5 millimeter to 10 millimeters, further preferably in the range of from 0.5 millimeter to 2 millimeters, particularly preferably in the region of 1 millimeter. Hereby a first part which can be pretensioned with little force can be provided. The wall thickness can be constant.

In the case of a solid or comparatively rigid, not particularly elastic embodiment variant, a thickness of the second part (fixing part) of the attachment is preferably in the range of from 0.5 to 10 millimeters, further preferably in the range of from 0.5 to 3 millimeters, particularly preferably in the region of 1 millimeter. The second part can have a constant wall thickness.

The wall thickness can be at least almost constant, preferably it is almost constant on the whole attachment. Thereby the attachment can be produced in a simple manner. It can be produced using an injection-molding process and, because of the equal wall thickness, the attachment can dry out at a uniform speed. In the case of a thinner wall thickness, the attachment can dry more quickly. For the case where the wall thickness is to vary, e.g. to provide an internal thread on the second part, the wall thickness preferably varies by not more than 50%, further preferably 20%, particularly preferably 10%.

Preferably the first part (contact part) of the attachment is designed film-like, i.e. with a wall thickness of less than 50 μm, preferably less than 30 μm, particularly preferably a wall thickness in the range of from 10 to 20 μm.

Particularly preferably the whole attachment is designed film-like. The attachment is made so thin-walled that the shell formed is made like a film with an inherent stability.

According to an embodiment example, the attachment is formed by a film which comes to rest substantially over the whole surface with the first part against the distal side of a contact lens and with the second part against a lateral surface of a contact lens.

Such a film can have a wall thickness in the micrometer range, e.g. in the two-digit or three-digit μm range. In order that the film can be removed manually, it is advantageous if it has a wall thickness at least in the two-digit or three-digit μm range. If the whole attachment is designed as a film, a wall thickness of less than 100 μm can be sufficient to give the film a sufficient inherent stability, with the result that it can also be pulled off without tearing. The wall thickness is preferably at least in the range of from 10 to 20 μm.

In the case of a film, the first part can be welded to a lens element in a vacuum method and the difference in pressure between atmospheric pressure in the surroundings and a more or less significant negative pressure at the interface can ensure that the first part comes to rest against a lens element without disruptive air gaps forming. Depending on the design of the film, air gaps can also be ruled out entirely. Independently thereof a liquid can be introduced at the interface. The second part can be weldable to a contact lens and the attachment can be formed completely from a coherent film.

By the expression substantially over the whole surface is meant that the first and second parts rest almost completely against a contact lens, e.g. are welded on, and only one section, e.g. on the second part, protrudes, by means of which the film can be gripped and pulled off again.

At least one of the objects named above is also achieved by a contact lens system, in particular an optoacoustic contact lens system, with a contact lens, in particular an optoacoustic contact lens, and with an attachment according to the invention. By optoacoustic contact lens is meant a contact lens with which acoustic vibrations can also be transferred, in particular to measure a temperature during a laser coagulation. By optoacoustic contact lens system is meant a contact lens system which has an optoacoustic receiver which can be integrated in the contact lens.

In the case of a contact lens system according to the invention the total optical transmission which can be achieved can reach more than 85% or even more than 95%, thus is particularly high. This is true in particular for a wavelength range of from 450 nm to 1100 nm, preferably 514 nm to 670 nm, further preferably 523 nm to 670 nm. For this wavelength range the contact lens system can have a particularly high transmission. The total acoustic transmission which can be achieved can reach more than 50% or even more than 85%, is therefore likewise advantageously high. This is true in particular for a frequency range of from 0.5 MHz to 20 MHz, preferably 0.8 MHz to 1.2 MHz. For this frequency range the contact lens system can have a particularly high transmission.

A free optical diameter of the contact lens system can be in the range of from 5 to 20 mm, preferably in the range of from 10 to 14 mm, further preferably in the region of 12.5 mm. Particularly preferably the free optical diameter is 12.5 mm. If the contact lens system has, e.g., an annular piezoceramic or an annular piezo sensor, the free optical diameter can at least almost correspond to the internal diameter of the piezoceramic or be delimited by it.

According to an embodiment example a liquid is introduced at an interface between the attachment and the contact lens or is already applied to the attachment before the attachment is placed on the contact lens.

The following materials are often used as materials for a (first) lens element of the contact lens: PMMA, quartz glass.

As materials for the first part or both parts of the attachment, or also only for the second part, e.g. the following materials are considered: PMMA (polymethyl methacrylate), quartz glass, polystyrene (PS), cycloolefin copolymers (COC), polycarbonate (PC). These materials can in principle be used in all embodiments of the attachment.

As liquids or gel-like fluids for an interspace, possibly unintentionally present or deliberately formed at the interface between contact lens and attachment, between the first part of the attachment and the first lens element, among other things the following liquids come into consideration: water, silicone oil, olive oil, baby oil, glycerol, NaCl, Methocel, or also mixtures thereof. With Methocel there is, e.g., the advantage of a good connection and ease of use, in particular due to the application before the attachment is placed on the contact lens.

It has been shown that with water a good compromise can be found between acoustic and optical demands. Suitable liquids can be gel-like. They can be provided as optical and/or acoustic immersion between the attachment and the contact lens. It has been shown that an optical refractive index of the liquid in the range of the refractive index of the adjacent lens element of the contact lens or of the adjacent first part of the attachment is advantageous, preferably an optical refractive index which is identical to the refractive indices of the adjacent components, or, if these are different, a refractive index lying between them.

Preferably an acoustic impedance of the liquid is in the range of the impedances of the adjacent components. It is preferably identical to them. For the case where the two components have different impedances, the impedance preferably lies between these values.

In the following, refractive indices (Table 1) and impedances (Table 2) are given for the materials and liquids that can be used by way of example in connection with a contact lens system.

TABLE 1

| Material | Refractive index [n] |
| --- | --- |
| PMMA | 1.492 |
| Quartz glass | 1.46 |
| Water | 1.33 |
| Air | 1 |

TABLE 2

| Material | Acoustic impedance [Z in rayl] |
| --- | --- |
| PMMA | $3.28 \times 10^6$ |
| Quartz glass | $12.1 \times 10^6$ |
| Water | $1.5 \times 10^6$ |
| Air | 413.5 |
| Silicone oil | $1.5 \times 10^6$ |
| Olive oil | $1.32 \times 10^6$ |
| Baby oil | $1.17 \times 10^6$ |
| Glycerol | $2.34 \times 10^6$ |

A contact lens system consisting of an attachment according to the invention as well as a contact lens can be provided by means of a method with the following steps:

providing an attachment according to the invention, in particular a sterile and/or disinfected attachment;

connecting a second part of the attachment to the contact lens in such a way that the second part can be manually removed from the contact lens again;

bringing a first part of the attachment and the contact lens into connection on a distal side of the contact lens, wherein the position of the first part on the distal side is determined by the second part, with the result that a bearing surface for an eye can be provided reversibly on the contact lens.

It is thus totally uncomplicated for a doctor or operator to use a contact lens when sterility is required but the contact lens itself is not sterile. The doctor or an assistant only has to connect the attachment to the contact lens, which can be ensured e.g. by screwing on or by a snap-on or click mechanism which can be assembled even more quickly or pulling on or welding of a film-like attachment.

In a further step, a liquid can be introduced at the interface between the first part and the lens element. Such a liquid is not absolutely necessary but can offer advantages in that it is possible more effectively to prevent air gaps from forming at the interface. The liquid can fill air gaps if any are still present despite a pretensioning. If the liquid is gel-like, e.g. like Methocel, it can also be applied inside the attachment in a simple manner before the attachment is fixed to the contact lens, without it running or dripping. The liquid can also be introduced on the distal side of the contact lens after the first part has been pretensioned. A liquid can also be introduced before a pretensioning if it can thereby be ensured that no self-contained cavities form.

Hereby an optically and/or acoustically neutral interface can be provided between the contact lens and the attachment or an eye. In a method according to the invention the attachment can be connected to the contact lens in such a way that a total optical transmission of more than 85%, particularly preferably more than 95% is achieved. By preventing air pockets, which can preferably be achieved by means of a liquid and/or a gel, a jump in or a discontinuity of an acoustic impedance or an optical refractive index is prevented at the individual boundary surfaces. Even in the case where form-fitting contact between attachment and contact lens may possibly not be over the whole surface, a jump in the refractive index or impedance can be prevented or at least kept small. Preferably a liquid and/or a gel is used which lead to such a total transmission for a wavelength range of from 450 nm to 1100 nm, preferably 514 nm to 670 nm, further preferably 523 nm to 670 nm.

According to an embodiment example, the attachment can also be connected to the contact lens in such a way that a total acoustic transmission of more than 50%, particularly preferably more than 85% is achieved.

According to an embodiment example, a liquid and/or a gel is used which lead to such a total transmission for a frequency range of from 0.5 MHz to 20 MHz, preferably 0.8 MHz to 1.2 MHz.

According to an embodiment example, the first part can be brought to rest against the distal side of the contact lens with a pretensioning by means of the second part, with the result that the first part rests flat against the distal side. This can result from the second part being connected to the contact lens in such a way that it is under tension and transfers a tensile force to the first part. If the first part is made with a geometry which differs from the distal side of the contact glass, the tensile force is preferably established to be so high that the first part is deformed until it takes on the geometry of the distal side of the contact glass and rests flat against the distal side. Hereby with a handgrip a sterile bearing surface which is optoacoustically compatible can be provided on the contact lens.

In order to use the contact lens for a further diagnosis and/or therapy, the attachment can be removed from the contact lens and replaced by an attachment which is already provided and if necessary sterilized and/or disinfected. The removal can take place in the following steps:

releasing the second part of the attachment;
by means of the release of the second part, removing the second and first part; and optionally and if necessary before releasing the second part:
removing a liquid introduced between the contact lens and the attachment.

The second part can be released by twisting off, pulling down, unclicking and/or unsnapping, depending on what connection means are provided.

The invention is explained in more detail using the following figures. Unless explicitly stated to the contrary, individual features of the embodiment examples shown in detail can in principle also be combined with each other.

In FIG. 1a a contact lens system 1 consisting of a contact lens 20 and an attachment 10 is shown. The contact lens has a first lens element 21 arranged on a distal side of the contact lens as well as a second lens element 22. An arrow Pd shown for the purposes of better understanding points in a distal direction, and an arrow Pp points in a proximal direction. The contact lens 20 has an outer casing surface 20a which here is designed conical and can be called lateral surface as it delimits the lateral extension of the contact lens. The contact lens 20 can be understood as a device with three main components, with a rotationally symmetrical outer casing surface 20a and lens elements 21, 22 arranged inside it.

On the distal side the contact lens 20 is provided with the attachment 10. The contact lens 20 and the attachment 10 can be made and arranged rotationally symmetrical in relation to an optical axis A. The attachment 10 follows the contour of the contact lens 20 and is present here as a device with a substantially constant wall thickness. The attachment 10 has two parts which are to be separated functionally, namely a first part 10a; 200a with optoacoustic compatibility and a second part 10b with a fixing function. The first part 10a rests against the distal side of the contact lens, here specifically against the distal lens element 21, and the second part 10b rests against the lateral surface 20a. The first and second parts are connected to each other and the attachment 10 can be made in one piece as an integral component. It can be seen that the attachment 10 has a small wall thickness in relation to its absolute dimensions. The wall thickness is substantially smaller than, e.g., the thickness of the distal lens element 21. The second part has an inner casing surface L1 and an outer casing surface L2.

The first part 10a is optoacoustically compatible in that it does not interfere with an optical beam path and/or acoustic vibrations. It is made from a transparent material or a material which is transmissible for the incident radiation. The first part 10a can come to rest substantially completely against the distal side, here a concave surface of the lens element 21. A liquid at the interface between the distal side of the contact lens 20 and the first part is not necessarily required. Air gaps or other interspaces which would degrade an optoacoustic compatibility can rather already be prevented by bringing the first part 10a to rest against the distal side with a pretensioning. A pretensioning can be generated by a force which is transferred from the second part 10b to the first part. In the case of an externally rotationally symmetrical contact lens, the second part can be screwed onto the contact lens 20 and, via the screw connection, a force can be transferred which acts on the first part in the proximal direction.

In other words, the first part 10a can be pulled onto the distal side of the contact lens 20. For this purpose, the second part can have an internal thread on the inner casing surface L1 and, on the outer casing surface L2, e.g., any type of profile, be it grooves, ridges or only a generally rough surface. The contact lens itself can be provided with an external thread on the lateral surface 20a. For the case where the contact lens 20 does not have a rotationally symmetrical external geometry, other types of connection can also be provided, e.g. a bayonet connection, or a click or snap-on mechanism formed by any projections or recesses. Any type of connection is advantageous which can prevent the attachment from twisting vis-à-vis the contact lens when an operator is working with the contact lens system on a patient. Also in the case of other movements of the contact lens 20, e.g. sliding or tilting, a fixing without the risk of a relative movement is desired. In principle, this can be ensured by means of any of the named types of connection. The second part can be connected to the contact lens via a click or snap-on connection 11.

In the embodiment example shown the reusability of the attachment 10 can also be improved in that the first part 10a, specifically a second side S2 of the first part 10a, has a curvature which is formed to be more pronounced than a curvature of the concave distal side, i.e. of the lens element 21. In other words, the second side S2 has a radius of curvature Rd2 which is smaller than a radius of curvature Rc of the lens element. Hereby the contact against the interface can initially be only punctiform but then, with the application of a pretensioning force via the second part 10b, become flat. It can thus be ensured that, even in the case of frequent sterilization, an attachment can be reused, even when it has been stressed and possibly minimally deformed by the sterilization.

The attachment 10 described just now has the advantage e.g. that it can be produced cost-effectively from a single material, in particular can be injection molded, and that changes to the optical properties of a contact lens do not have to be carried out when the attachment 10 is used, in order to ensure sterility. The attachment 10 can be understood as a sterile and/or disinfected replaceable cap which is reusable or is used as a single-use product. Depending on the number of pieces and the choice of material, the attachment 10 can even be produced so cost-effectively that it is more advantageous to use it once than to sterilize and/or disinfect the entire contact lens. In principle, the attachment 10 is, however, provided to be used and thus also sterilized and/or disinfected even multiple times. It is substantially easier and more cost-effective to sterilize and/or disinfect the attachment 10 than to sterilize or disinfect the entire contact lens.

Figure 1B:
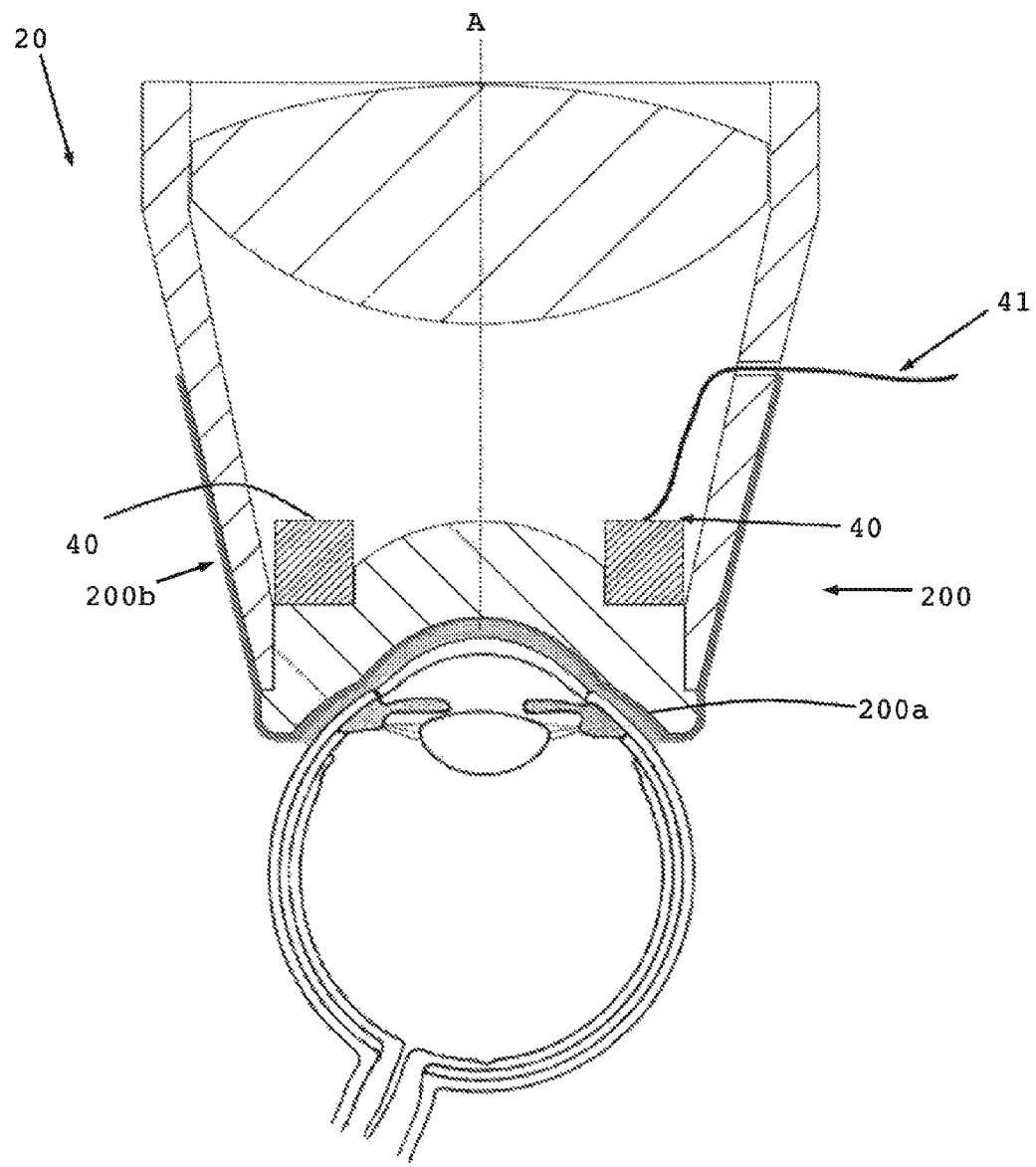
FIG. 1b is a schematic sectional view of the embodiment example shown in FIG. 1a, wherein the contact lens is provided with piezo sensors.

In FIG. 1b an optoacoustic contact lens 20 is shown which is provided with piezo sensors 40. The piezo sensors 40 are arranged within the contact lens 20 and are supplied with power via an electric wire 41, in particular a cable. By means of these piezo sensors 40, an integrated acoustic measuring system can be provided to detect acoustic vibrations and to derive therefrom a temperature and to control a (laser) therapy based on the derived temperature values. Such a contact lens 20 can only be sterilized and/or disinfected in a very expensive way and the sensors and the electrics would be affected by that. A sterile and/or disinfected attachment 10 according to the invention can therefore lead to particularly great advantages in this type of contact lenses.

In this embodiment example the attachment 200 only has a wall thickness in the micrometer range. Such an attachment can be designed as a film. With regard to a single use there are further cost advantages vis-à-vis the attachment 20 previously described in FIG. 1a which can be connected reversibly. A film 200 can be applied, in particular welded, to the outside of the contact lens 20 using a sterile-functioning vacuum-packing system. By means of the pressure difference at the interface to the distal side of the contact lens 20, it can be ensured that the film 200 rests with the first part (contact part) 200a completely against the distal side. The fixing part 200b rests against the outer surface of the contact lens and prevents the contact part 200a of the film-like attachment 200 from slipping. The film thickness here is between 10 and 100 μm, in particular a specific value from this range.

Figure 2A:
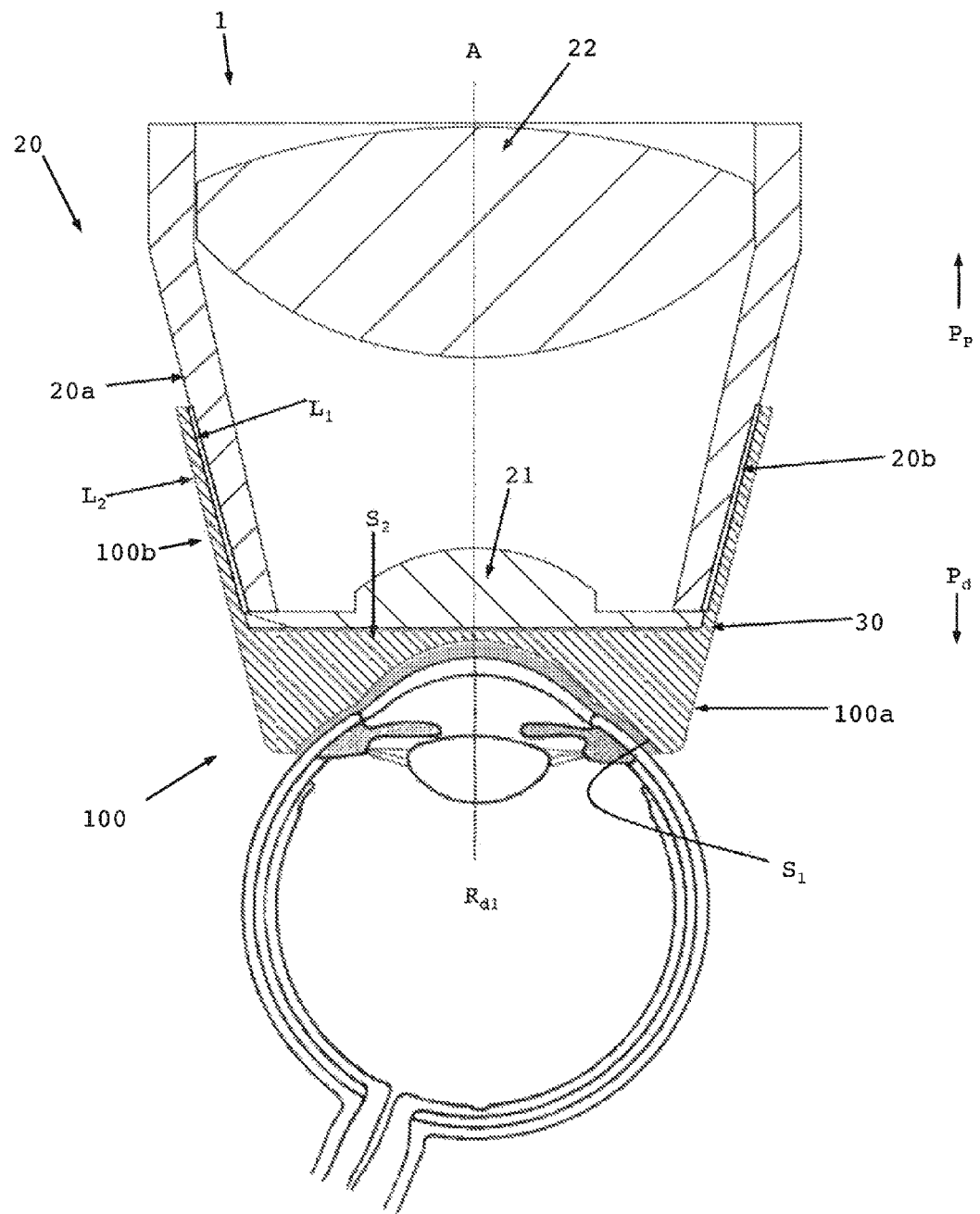
FIG. 2a is a schematic sectional view of an attachment according to a second embodiment example of the invention, wherein the attachment is arranged on a contact lens and an eye is in contact with the attachment.

In FIG. 2a substantially the same components of a contact lens system 1 are shown as in FIG. 1a, except that the attachment 100 is a device with a varying thickness or wall thickness, in particular because not only is the first part 100a of the attachment 100 optoacoustically compatible, but it also takes on an optical function and can be understood as part of the lens system of the contact lens 20. A first side S1 of the first part 100a is designed concave to receive an eye resting against it. The curvature of the first side S1 can be described by a radius of curvature Rd1. In this respect there is agreement with the embodiment example shown in FIGS. 1a and 1b. A second side S2 is, however, not markedly curved and also not designed convex or concave but is substantially planar and also the distal side of the contact lens 20 is made substantially planar. A simple geometric interface can hereby be provided.

At the interface between the first part 100a and the distal side a liquid 30 can optionally be provided. Although the two surfaces adjacent to each other at the interface are shown planar, one of the two or both can have a slight curvature, with the result that, as described in connection with FIG. 1a, a flat contact can be established by means of a pretensioning force. The difference between the curvatures or the radii of curvature (not shown because the center of curvature would lie far outside the area of the drawing) is however smaller than in the first embodiment example, in particular because the attachment 100, as an inherently more stable part, is to be elastically deformable only in a smaller area.

The contact lens has an externally rotationally symmetrical lateral surface 20a, onto which the attachment is screwed. For this purpose an external thread 20b is provided on the lateral surface 20a, and a force which acts on the first part in the proximal direction can be established and transferred via the screw connection. In other words, the first part 100a can be pulled onto the distal side of the contact lens 20. For this purpose, the second part can have an internal thread on the inner casing surface L1 and, on the outer casing surface L2, e.g., any type of profile, be it grooves, ridges or only a generally rough surface. In particular, for the case where the contact lens 20 does not have a rotationally symmetrical external geometry, other types of connection can also be provided, e.g. a bayonet connection, or a click or snap-on mechanism formed by any projections or recesses. Any type of connection is advantageous which can prevent the attachment from twisting vis-à-vis the contact lens when an operator is working with the contact lens system on a patient. Also in the case of other movements of the contact lens 20, e.g. sliding or tilting, a fixing without the risk of a relative movement is desired. In principle this can be ensured by means of any of the named types of connection.

Figure 2B:
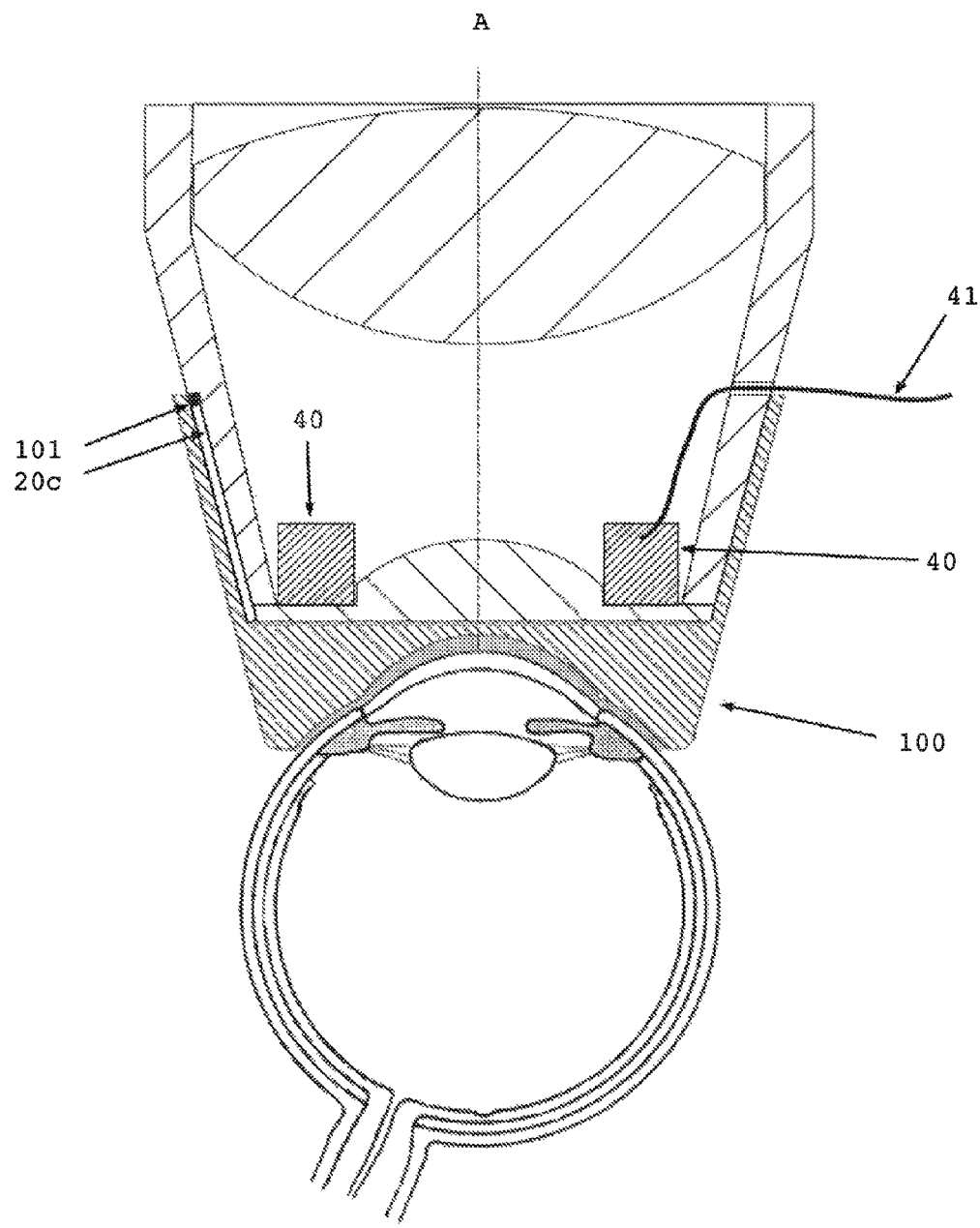
FIG. 2b is a schematic sectional view of the embodiment example shown in FIG. 2a, wherein the contact lens is provided with piezo sensors.

In FIG. 2b a contact lens 20 is shown which is provided with piezo sensors 40. The piezo sensors 40 are arranged within the contact lens 20 and are supplied with power via an electric wire 41, in particular a cable. A sterile attachment 10 according to the invention can lead to particularly great advantages in this type of contact lenses for the reasons already named above. The attachment 100 is guided in a groove 20c for a bayonet connection and secured by a detent 101. Furthermore it can be seen that the piezo sensors 40 can be arranged in the immediate vicinity of the attachment 10, whereby further advantages can result such as e.g. a more accurate or quicker detection of acoustic vibrations and thus also temperature measurement, depending on the choice of the material of the attachment. A reliable temperature measurement is very important e.g. in connection with laser systems for coagulation as the course of the therapy is to be controlled by the temperature measurement.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMBERS

1 Contact lens system
10, 100, 200 Attachment
10a, 100a, 200a First part (contact part), in particular optoacoustically compatible part
10b, 100b, 200b Second part, in particular fixing part
11 Click or snap-on connection
101 Detent for bayonet connection
20 Contact lens
20a Lateral surface, in particular outer casing surface
20b External thread on the contact lens
20c Groove for bayonet connection
21 Distal side of the contact lens, in particular with first lens element
22 Proximal side of the contact lens, in particular with second lens element
30 Liquid in the area of the interface between contact lens and attachment
A Optical axis of the contact lens
40 Detectors, in particular piezo sensors
41 Electrical connection, in particular cable
L1 Inner casing surface of the second part
L2 Outer casing surface of the second part
Pd Arrow pointing in the distal direction
Pp Arrow pointing in the proximal direction
Rc Radius of the concave surface of a lens element
Rd1 Radius of the first side of the first part of the attachment
Rd2 Radius of the second side of the first part of the attachment
S1 First side of the first part
S2 Second side of the first part

The invention claimed is:

1. An attachment for a contact lens, the attachment comprising:
 a first part provided to be held in position against an eye; and
 a second part connected to the first part, the second part for fixing the attachment to a contact lens;
 wherein the first part corresponds to a distal side of the contact lens and forms at least one of a sterile or a disinfected bearing surface for the eye, and wherein the second part is configured to connect the attachment to the contact lens and to bring the first part to rest against a distal side of a surface of a lens element of the contact lens, and
 wherein the first part is formed to abut the contact lens with a pretensioning transferred from the second part to the first part or with a negative pressure.

2. The attachment according to claim 1, wherein the attachment is a cap which, with the first part and with the second part, is configured to rest against the contact lens.

3. The attachment according to claim 1, wherein the attachment is a cap with the first part having a varying thickness in a distal direction.

4. The attachment according to claim 3, wherein the attachment has a substantially planar proximal side on the first part.

5. The attachment according to claim 1, wherein the attachment has, in the first part, a wall thickness which is smaller than 10 millimeters.

6. The attachment according to claim 5, wherein the attachment is formed by a film which is configured to rest substantially over the whole bearing surface with the first part against the distal side of the contact lens and with the second part against a lateral surface of the contact lens.

7. A contact lens system with a contact lens, in particular an optoacoustic contact lens for at least one of eye diagnosis or therapy, and with an attachment comprising:
 a first part provided to be held in position against an eye; and
 a second part connected to the first part, the second part for fixing the attachment to a contact lens;
 wherein the first part corresponds to a distal side of a contact lens and forms at least one of a sterile or a disinfected bearing surface for the eye, and wherein the second part is configured to connect the attachment to the contact lens and to bring the first part to rest against a distal side of a surface of a lens element of the contact lens, and
 wherein the first part is formed to abut the contact lens with a pretensioning transferred from the second part to the first part or with a negative pressure.

8. The contact lens system according to claim 7, wherein a liquid is introduced at an interface between the attachment and the contact lens.

9. A method for producing a contact lens system consisting of an attachment and a contact lens, the method comprising:
 providing an attachment including a first part provided to be held in position against an eye, and a second part connected to the first part, the second part for fixing the attachment to the contact lens, wherein the first part corresponds to a distal side of the contact lens and forms at least one of a sterile or a disinfected bearing surface for the eye, and wherein the second part is configured to connect the attachment to the contact lens and to bring the first part to rest against a distal side of a surface of a lens element of the contact lens;
 connecting the second part of the attachment to the contact lens such that the second part is configured to be manually removed from the contact lens again;
 bringing the first part of the attachment and the contact lens into connection on the distal side of the contact lens, wherein the position of the first part on the distal side is determined by the second part, with the result that the bearing surface for the eye can be provided reversibly on the contact lens,
 wherein the first part is formed to abut the contact lens with a pretensioning transferred from the second part to the first part or with a negative pressure.

10. The method according to claim 9, further comprising bringing the first part to rest against the distal side of the contact lens with the pretensioning via the second part, with the result that the first part rests flat against the distal side.

11. The method according to claim 10 further comprising using at least one of a liquid or a gel which lead to the high transmission for a frequency range of 0.8 MHz to 1.2 MHz.

12. The method according to claim 9 further comprising connecting the attachment to the contact lens such that a total acoustic transmission of more than 85 percent is achieved.

13. A method for producing a contact lens system consisting of an attachment and a contact lens, the method comprising:
- providing an attachment including a first part provided to be held in position against an eye, and a second part connected to the first part, the second part for fixing the attachment to a contact lens, wherein the first part corresponds to a distal side of a contact lens and forms at least one of a sterile or a disinfected bearing surface for the eye, and wherein the second part is configured to connect the attachment to the contact lens and to bring the first part to rest against a distal side of the contact lens;
- connecting the second part of the attachment to the contact lens such that the second part is configured to be manually removed from the contact lens again;
- bringing the first part of the attachment and the contact lens into connection on a distal side of the contact lens, wherein the position of the first part on the distal side is determined by the second part, with the result that the bearing surface for the eye can be provided reversibly on the contact lens; and
- connecting the attachment to the contact lens such that a total acoustic transmission of more than 50 percent is achieved.

14. A method for producing a contact lens system consisting of an attachment and a contact lens, the method comprising:
- providing an attachment including a first part provided to be held in position against an eye, and a second part connected to the first part, the second part for fixing the attachment to a contact lens, wherein the first part corresponds to a distal side of a contact lens and forms at least one of a sterile or a disinfected bearing surface for the eye, and wherein the second part is configured to connect the attachment to the contact lens and to bring the first part to rest against a distal side of the contact lens;
- connecting the second part of the attachment to the contact lens such that the second part is configured to be manually removed from the contact lens again;
- bringing the first part of the attachment and the contact lens into connection on a distal side of the contact lens, wherein the position of the first part on the distal side is determined by the second part, with the result that the bearing surface for the eye can be provided reversibly on the contact lens;
- bringing the first part to rest against the distal side of the contact lens with a pretensioning via the second part, with the result that the first part rests flat against the distal side; and
- using at least one of a liquid or a gel which leads to the high transmission for a frequency range of 0.5 MHz to 20 MHz.

* * * * *